United States Patent [19]

Meyer et al.

[11] Patent Number: 4,769,375
[45] Date of Patent: Sep. 6, 1988

[54] CIRCULATION-ACTIVE 1,4-DIHYDROPYRIDINE DERIVATIVES AND USE THEREAS

[75] Inventors: Horst Meyer; Gerhard Franckowiak, both of Wuppertal, Fed. Rep. of Germany; Günther Thomas, Garbagnate, Italy; Matthias Schramm, Cologne, Fed. Rep. of Germany; Michael Kayser, Hagen, Fed. Rep. of Germany; Martin Bechem; Rainer Gross, both of Wuppertal, Fed. Rep. of Germany

[73] Assignee: Bayer Aktiengesellschaft, Leverkusen, Fed. Rep. of Germany

[21] Appl. No.: 890,998

[22] Filed: Jul. 25, 1986

[30] Foreign Application Priority Data

Aug. 9, 1985 [DE] Fed. Rep. of Germany ...... 3528602

[51] Int. Cl.$^4$ .................. A61K 31/47; C07D 101/04; C07D 215/18; C07D 215/24
[52] U.S. Cl. .................... 514/311; 514/314; 546/167; 546/170; 546/173; 546/178; 544/333
[58] Field of Search ............... 546/170, 173, 167, 178; 514/311, 314

[56] References Cited

FOREIGN PATENT DOCUMENTS 0071819 2/1983 European Pat. Off. .
2018738 10/1971 Fed. Rep. of Germany .

OTHER PUBLICATIONS

Bulletin of the Chemical Society of Japan; vol. 42; No. 1; pp. 220-223; A. Sakurai et al.

Primary Examiner—Glennon H. Hollrah
Assistant Examiner—D. B. Springer
Attorney, Agent, or Firm—Sprung Horn Kramer & Woods

[57] ABSTRACT

Circulation-active dihydropyridines of the formula

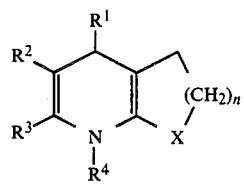

in which
$R^1$ is optionally substituted aryl or heterocyclic,
$R^2$ is H, $NO_2$, CN, $C_1$–$C_8$-alkylsulphonyl, aryl or carboalkoxy,
$R^3$ is alkyl or aryl,
$R^4$ is H or alkyl,
X is C=O or a direct bond, and
n is a number from 1 to 20, or physiologically acceptable salts thereof. A synthesis using morpholines or thiomorpholines is also disclosed.

14 Claims, No Drawings

CIRCULATION-ACTIVE 1,4-DIHYDROPYRIDINE DERIVATIVES AND USE THEREAS

The invention relates to new 1,4-dihydropyridine derivatives, a process for their preparation and their use in medicaments, in particular in medicaments which influence the circulation.

It is known that reaction of benzylidenecyclohexanone and morpholinocyclohexene gives a cyclo-adduct which, on hydrolysis and subsequent treatment with ammonia, does not give dihydropyridine but only its oxidation product [I. W. Lewis, P. L. Meyers, M. I. Readhead, J. Chem. Soc. (1970), 771].

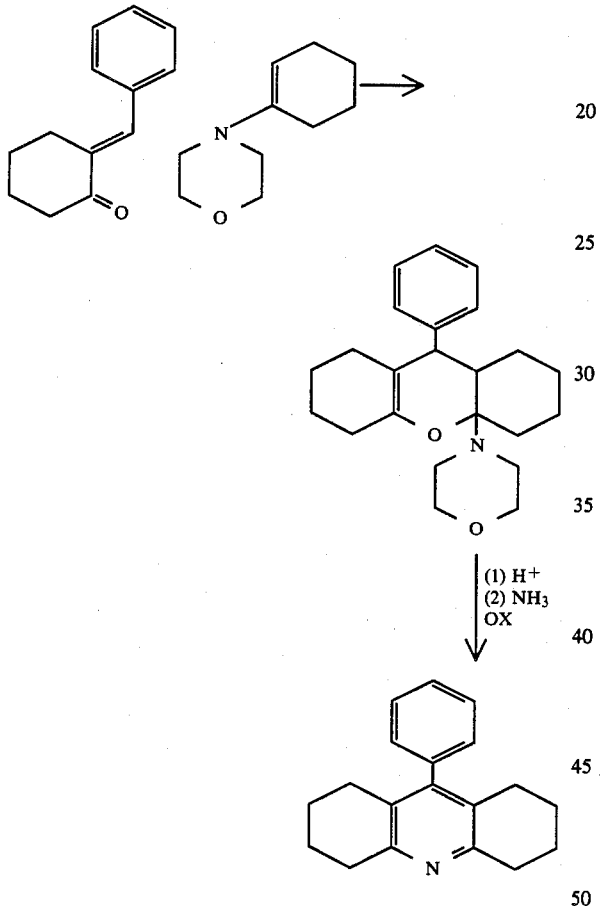

The invention relates to dihydropyridines of the general formula (I)

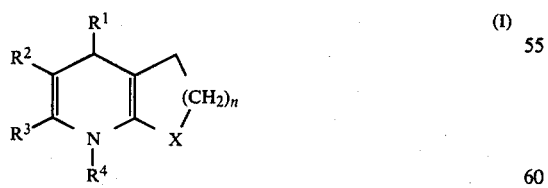

in which
R¹ represents aryl ($C_6-C_{12}$) or a heterocyclic radical from the series comprising thienyl, furyl, pyrryl, pyrazolyl, imidazolyl, oxazolyl, isoxazolyl, thiazolyl, thiadiazolyl, pyridyl, pyridazinyl, pyrimidyl, pyrazinyl, indolyl, benzimidazolyl, benzoxazolyl, benzothiazolyl, quinolyl, isoquinolyl, quinazolyl, quinoxalyl, thionaphthenyl, chromenyl, thiochromenyl, benzoxadiazolyl and benzothiadiazolyl, the aryl radical and the heterocyclic radicals optionally containing 1 to 3 identical or different substituents from the group comprising $C_1-C_8$-alkyl, $C_1-C_8$-alkoxy, $C_1-C_8$-alkylthio, halogen, nitro, cyano, trifluoromethyl, $C_1-C_8$-monofluoroalkoxy, $C_1-C_8$-polyfluoroalkoxy, hydroxyl, amino, $C_1-C_6$-alkylamino, di-$C_1-C_6$-alkylamino, carboxyl, $C_1-C_6$-alkoxycarbonyl, phenyl, benzyl, benzyloxy or benzylthio, or represents straight-chain, branched or cyclic $C_1-C_8$-alkyl which is optionally substituted by thienyl, furyl, pyridyl or pyrimidyl, R² represents hydrogen, nitro, cyano or $C_1-C_8$-alkylsulphonyl, or represents the group $$-\underset{\underset{O}{\|}}{C}-R^5$$

wherein
R⁵ represents straight-chain, branched or cyclic $C_1-C_8$-alkyl, or represents a group of the formula —O—R⁶,
wherein
R⁶ represents straight-chain, branched or cyclic $C_1-C_{10}$-alkyl, which is optionally interrupted in the chain by one or two oxygen and/or sulphur atoms and which is optionally substituted by one or more halogens, hydroxyl, cyano, nitro, phenyl or pyridyl, or by an amino group, this amino group optionally being mono- or disubstituted by identical or different substituents from the group comprising $C_1-C_6$-alkyl, $C_6-C_{10}$-aryl and $C_7-C_{14}$-aralkyl, R³ represents $C_6-C_{12}$-aryl, or represents straight-chain or branched $C_1-C_8$-alkyl, which is optionally substituted by hydroxyl, halogen or $C_2-C_7$-acyloxy, R⁴ represents hydrogen, or represents straight-chain, branched or cyclic $C_1-C_8$-alkyl, X represents the group $$\underset{/}{\overset{\backslash}{\phantom{-}}}C=O,$$

or represents a direct bond and
n represents a number from 1 to 20, in the form of their isomers, isomer mixtures, racemates, optical antipodes and their physiologically acceptable salts.

Compounds of the general formula (I) which are of particular interest are those in which
R¹ represents phenyl, or represents thienyl, furyl, imidazolyl, oxazolyl, thiazolyl, pyridyl, pyrimidyl, quinolyl, benzimidazolyl, benzoxazolyl, benzothiazolyl, thiochromenyl or benzoxadiazolyl, the phenyl and the heterocyclic radicals optionally containing 1 or 2 identical or different substituents from the group comprising $C_1-C_6$-alkyl, $C_1-C_6$-alkoxy, $C_1-C_6$-alkylthio, fluorine, chlorine, bromine, nitro, cyano, trifluoromethyl, $C_1-C_4$-monofluoroalkoxy, $C_1-C_4$-polyfluoroalkoxy, hydroxyl, amino, $C_1$–$C_3$-alkylamino, di-$C_1$–$C_3$-alkylamino, carboxyl, $C_1$–$C_4$-alkoxycarbonyl, phenyl, benzyl, benzyloxy or benzylthio, or represents straight-chain, branched or cyclic $C_1$–$C_6$-alkyl which is optionally substituted by pyridyl or pyrimidyl, $R^2$ represents hydrogen, nitro, cyano or $C_1$–$C_6$-alkyl-sulphonyl, or represents the group

wherein $R^5$ represents straight-chain, branched or cyclic $C_1$–$C_6$-alkyl, or represents a group of the formula —O—$R^6$, wherein $R^6$ represents straight-chain, branched or cyclic $C_1$–$C_8$-alkyl, which is optionally interrupted in the chain by one or two oxygen atoms and which is optionally substituted by one or more fluorine, chlorine, bromine, hydroxyl, cyano, nitro, phenyl or pyridyl groups or by an amino group, this amino group optionally being mono- or di-substituted by identical or different substituents from the group comprising $C_1$–$C_4$-alkyl, phenyl or benzyl, $R^3$ represents phenyl, or represents straight-chain or branched $C_1$–$C_6$-alkyl, which is optionally substituted by hydroxyl or one or more fluorine, chlorine, bromine or $C_2$–$C_5$-acyloxy groups, $R^4$ represents hydrogen, or represents straight-chain or branched or cyclic $C_1$–$C_6$-alkyl, X represents the group

or represents a direct bond and n represents a number from 1 to 16, in the form of their isomers, isomer mixtures, racemates, optical antipodes and their physiologically acceptable salts.

Particularly preferred compounds of the general formula (I) are those in which $R^1$ represents phenyl, thienyl, furyl, pyridyl, pyrimidyl, benzoxadiazolyl or thiochromenyl, the radicals mentioned optionally containing 1 or 2 identical or different substituents from the group comprising $C_1$–$C_4$-alkyl, $C_1$–$C_4$-alkoxy, $C_1$–$C_4$-alkylthio, fluorine, chlorine, nitro, cyano, hydroxyl, trifluoromethyl, trifluoromethoxy, difluoromethoxy, fluoromethoxy, phenyl, benzyl, benzyloxy and benzylthio, $R^2$ represents hydrogen, nitro, cyano or $C_1$–$C_4$-alkyl-sulphonyl, or represents the group

wherein $R^5$ represents straight-chain or branched $C_1$–$C_4$-alkyl, or represents a group of the formula —O—$R^6$, wherein $R^6$ represents straight-chain, branched or cyclic $C_1$–$C_6$-alkyl, which is optionally interrupted in the chain by an oxygen atom and which is optionally substituted by one or more fluorine, hydroxyl, cyano, phenyl or N-benzyl-N-methylamino groups, $R^3$ represents phenyl, or represents straight-chain or branched $C_1$–$C_4$-alkyl, which is optionally substituted by hydroxyl, chlorine, bromine or acetyloxy, $R^4$ represents hydrogen, or represents straight-chain or branched $C_1$–$C_4$-alkyl, X represents the group

or represents a direct bond and n represents a number from 1 to 12, in the form of their isomers, isomer mixtures, racemates, optical antipodes and their physiologically acceptable salts.

Physiologically acceptable salts of the substances according to the invention can be salts with inorganic or organic acids. Examples which may be mentioned are: halides, such as bromides and chlorides, hydrogen sulphates, sulphates, hydrogen phosphates, acetates, maleates, fumarates, citrates, tartrates, lactates or benzoates.

The compounds according to the invention exist in stereoisomeric forms which either behave as mirror images (enantiomers) or do not behave as mirror images (diastereomers). The invention relates both to the antipodes and to the racemic forms as well as diastereomer mixtures. The racemic forms as well as the diastereomers can be separated into the stereoisomerically uniform constituents in a known manner (compare E. L. Eliel, Stereochemistry of Carbon Compounds, McGraw Hill, 1962).

The compounds of the formula (I) according to the invention can be prepared by a process in which benzylidene compounds of the general formula II

in which $R^1$–$R^3$ have the abovementioned meaning, and enamines of the general formula (III)

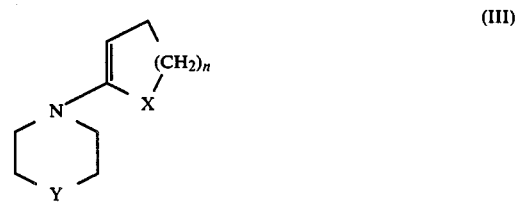

in which

X and n have the abovementioned meaning and

Y represents a direct bond, or represents oxygen, sulphur, amino or $C_1$–$C_4$-alkylamino, or represents a methylene chain with 1 or 2 carbon atoms, are reacted, if appropriate in the presence of water and/or inert organic solvents, to give the intermediate products of the general formula (IV)

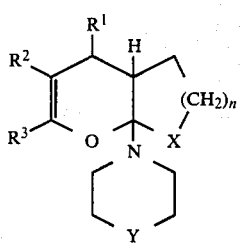
(IV)

in which
R¹–R³, X, Y and n have the abovementioned meaning,
and the intermediate products (IV) are reacted with acids and amines of the general formula (V)

$$R^4-NH_2 \quad (V)$$

in which
R⁴ has the abovementioned meaning, or with addition products thereof, if appropriate in the presence of water and/or inert organic solvents.

If methyl benzylideneacetoacetate, morpholinocyclohexene and ammonia are used as starting substances, the course of the reaction can be illustrated by the following equation:

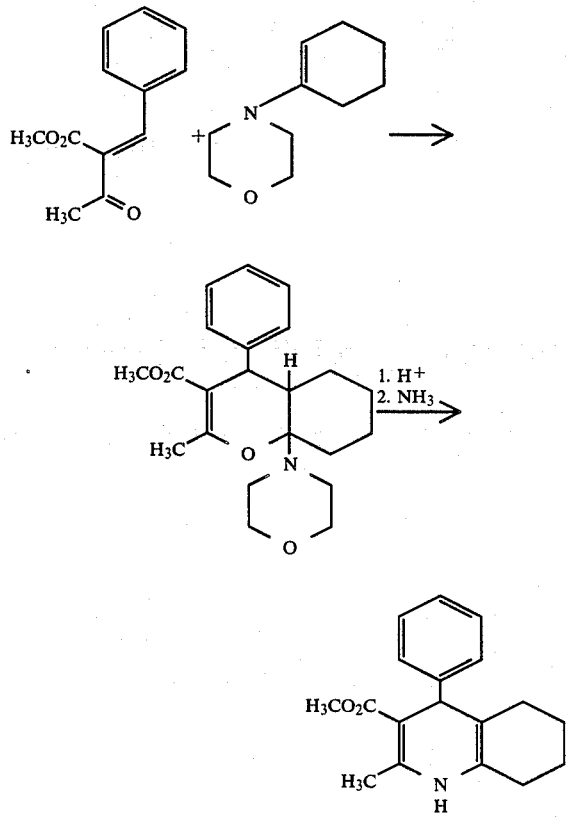

In view of Lewis et al, supra, it is surprising that reaction or cyclic tertiary enamines with benzylideneacetoacetic acid esters or benzylidenenitroacetones gives 1,4-dihydropyridine derivatives which are stable under the experimental conditions and are not oxidized to the corresponding pyridines.

The benzylidene compounds of the general formula (II) used as starting substances are known or can be prepared by methods which are known from the literature [compare G. Jones "The Knoevenagel Kondensation" in Organic Reactions XV, 204 (1967), and A. Dornow, W. Sassenberg, Liebigs Ann. Chem. 602, 14 (1957)].

The enamines of the general formula (III) used as starting substances are known or can be prepared by methods which are known from the literature [compare J. Szmuszkovicz "Enamines", Adv. Org. Chem. 4, 1 (1963, A. G. Cook "Enamines—Synthesis, Structure and Reactions", M. Dekker, New York 1969, and H. O. House "Modern Synthetic Reactions", 2nd edition, page 570, W. A. Benjamin Inc. Menlo Park, 1972].

The amines of the general formula (V) are known. Suitable acid addition products can be salts of the amines (V) with inorganic or organic acids, such as, for example, bromides, chlorides, hydrogen sulphates, sulphates, hydrogen phosphates, acetates, carbonates or bicarbonates.

The intermediate products IV formed in carrying out the process according to the invention are new. However, it is not necessary to isolate them.

Possible solvents both for the preparation of the intermediate products and for the preparation of the end products are water or all the inert organic solvents. These include, preferably, alcohols, such as methanol, ethanol, propanol or isopropanol, ethers, such as diethyl ether, dioxane, tetrahydrofuran and glycol monomethyl or dimethyl ether, dimethylformamide, dimethylsulphoxide, acetonitrile, ethyl acetate, hexamethylphosphoric acid triamide, pyridine, halogenohydrocarbons, such as methylene chloride, chloroform, carbon tetrachloride, dichloroethane or trichloroethyl and aromatic hydrocarbons, such as benzene, toluene or xylene. However, it is also possible to use mixtures of the solvents mentioned.

The customary inorganic or organic acids can be used as the acids. These include, preferably, hydrogen halides, such as hydrogen chloride or hydrogen bromide, sulphuric acid or phosphoric acid, or organic acids, such as acetic acid, propionic acid or tartaric acid, or sulphonic acids, such as, for example, methane-, ethane-, benzene- or toluenesulphonic acid.

The reaction temperatures can be varied within a relatively wide range. The reaction is in general carried out in a temperature range from 0° C. to 200° C., preferably from 10° C. to 150° C.

The process according to the invention is in general carried out under normal pressure. However, it is also possible to carry out the process under reduced pressure or under increased pressure.

In general, 0.5–5, preferably 1–2, moles of enamine III are employed per mole of benzylidene compound II. In general, 0.1–10 moles, preferably 0.5–5 moles, of acid are employed per mole of the intermediate compound. The amine V is in general used in an amount of 0.1–10, preferably 0.5–5, moles per mole of intermediate compound.

Various process variants are possible for the reaction of the intermediate products to give the dihydropyridines according to the invention. In variant A, first acid and then amine is added to the intermediate product, in variant B, first amine and then acid is added, and in variant C, amine and acid are added in the form of the addition product of the acid on the amine.

The substances of the formula (I) according to the invention display a useful pharmacological action spectrum. They influence the circulation, the contraction force of the heart, vascular tone and the tone of smooth muscles. They can therefore be used in medicaments, for example for treatment of circulatory diseases, coronary heart diseases and cardiac insufficiency. They can furthermore influence the blood sugar and can thus be used as therapeutics for metabolic diseases.

The cardiac and vascular actions were found on isolated perfused hearts of guineapigs. For this, the hearts of albino guineapigs weighing 250 to 350 g are used. The animals are sacrificed by a blow on the head, the thorax is opened, a metal cannula is inserted into the exposed aorta and the left auricle is opened. The heart is removed from the thorax with the lungs and connected to the perfusion apparatus via the aorta cannula under continuous perfusion. The lungs are removed at the roots of the lungs. Krebs-Henseleit solution (1) (118.5 mmol/l of NaCl, 4.75 mmol/l of KCl, 1.19 mmol/l of $KH_2PO_4$, 119 mmol/l of $MgSO_4$, 25 mmol/l of $NaHCO_3$ and 0.013 mmol/l of NaEDTA), the $CaCl_2$ content of which is varied as required but is as a rule 1.2 mmol/l, is used as the perfusion medium. 10 mmol/l of glucose are added as a substrate which supplies energy. Before the perfusion, the solution is filtered free from particles. The solution is gassed with carbogen (95% of $O_2$, 5% of $CO_2$, to maintain the pH value of 7.4). The hearts are perfused at a constant flow (10 ml/minute) at 32° C. by means of a roller squeezing pump.

To measure the cardiac function, a latex balloon filled with liquid and connected to a pressure transducer via a column of liquid is introduced through the left auricle into the left ventricle and the isovolumetric contractions are recorded on a high-speed recorder (Opie, 1., J. Physiol. 180 (1965) 529-541). The perfusion pressure is recorded by means of a pressure transducer connected to the perfusion system upstream of the heart. Under these conditions, a reduction in the perfusion pressure indicates coronary dilation, and an increase in the left ventricular pressure amplitude indicates an increase in the contractility of the heart. The compounds according to the invention are infused in suitable dilutions into the perfusion system a short distance upstream of the isolated heart.

The effects of some examples on the contractility and coronary resistance on isolated perfused guineapig hearts are shown in the following table.

| Example No. | Percentage change in the coronary resistance | | | Percentage change in the contractility at | | |
|---|---|---|---|---|---|---|
| | $10^{-7}$ | $10^{-6}$ | $10^{-5}$ | $10^{-7}$ | $10^{-6}$ | $10^{-5}$ g/ml |
| 8 | −8 | −35 | −35 | 0 | −42 | −85 |
| 9 | −23 | −43 | −48 | +13 | −74 | −98 |
| 32 | −7 | −21 | −21 | −8 | −68 | −95 |
| 33 | −4 | −29 | −41 | 0 | 0 | −52 |

The new active compounds can be converted in a known manner into the customary formulations, such as tablets, capsules, dragees, pills, granules, aerosols, syrups, emulsions, suspensions and solutions, using inert, non-toxic, pharmaceutically suitable excipients or solvents. The therapeutically active compound should in each case be present here in a concentration of about 0.5 to 90% by weight of the total mixture, that is to say in amounts which are sufficient to achieve the stated dosage range.

The formulations are prepared, for example, by extending the active compounds with solvents and/or excipients, if appropriate using emulsifying agents and/or dispersing agents, and, for example, in the case of the use of water as diluents, organic solvents can be used, if appropriate, as auxiliary solvents.

Examples of auxiliaries which may be mentioned are: water, non-toxic organic solvents, such as paraffins (for example petroleum fractions), vegetable oils (for example groundnut oil/sesame oil), alcohols (for example ethyl alcohol and glycerol) and glycols (for example propylene glycol and polyethylene glycol), solid excipients, such as, for example, ground natural minerals (for example kaolins, aluminas, talc and chalk), ground synthetic minerals (for example highly disperse silicic acid and silicates), sugars (for example sucrose, lactose and glucose), emulsifying agents (for example polyoxyethylene fatty acid esters and polyoxyethylene fatty alcohol ethers), binding agents for example (lignin, sulphite waste liquors, methylcellulose, starch and polyvinylpyrrolidone) and lubricants (for example magnesium stearate, talc, stearic acid and sodium sulphate).

Administration is effected in the customary manner, preferably orally or parenterally, in particular perlingually or intravenously. In the case of oral use, tablets can of course also contain, in addition to the excipients mentioned, additives such as sodium citrate, calcium carbonate and dicalcium phosphate, together with various additives, such as starch, preferably potato starch, gelatine and the like. Lubricants, such as magnesium stearate, sodium lauryl sulphate and talc, can furthermore be co-used for tablet-making. In the case of aqueous suspensions and/or elixirs intended for oral use, various flavour-improving agents or colorants can be added to the active compounds, in addition to the abovementioned auxiliaries.

In the case of parenteral use, solutions of the active compounds can be employed, using suitable liquid excipient materials.

In general, it has proved advantageous in the case of intravenous administration to administer amounts of about 0.001 to 1 mg/kg, preferably about 0.01 to 0.5 mg/kg of body weight, to achieve effective results, and in the case of oral administration the dosage is about 0.01 to 20 mg/kg, preferably 0.1 to 10 mg/kg of body weight.

Nevertheless, it may be necessary to deviate from the amounts mentioned, and in particular to do so as a function of the body weight of the experimental animal or of the nature of the administration, but also on the basis of the animal species and its individual behavior towards the medicament or the nature thereof, of its formulation and the time or interval at which administration takes place. Thus it can in some cases be sufficient to manage with less than the abovementioned minimum amount, while in other cases the upper limit mentioned must be exceeded. When relatively large amounts are administered, it may be advisable to divide these into several individual doses over the course of the day. The same dosage range is envisaged for administration in human medicine. The above statements also apply here in the general sense.

PREPARATION EXAMPLES

Example 1

Ethyl 8a-morpholino-4-(3-nitrophenyl)-2-phenyl-4a,5,6,7,8,8a-hexahydro-4H-chromene-3-carboxylate

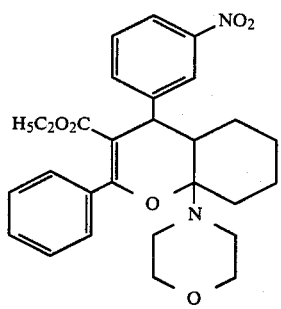

A solution of 10.9 g (0.033 mole) of ethyl 3-nitrobenzylidenebenzoylacetoacetate and 5.6 g (0.033 mole) of morpholinocyclohexane in 80 ml of ethanol is boiled under reflux for 4 hours. The solution is concentrated and the residue is triturated with ether, filtered off with suction and recrystallized from ethanol.

Yield: 7.3 g (44.5% of theory).
Melting point: 134°–136° C.

Example 2

Ethyl 2-phenyl-4-(3-nitrophenyl)-1,4,5,6,7,8-hexahydroquinoline-3-carboxylate (variant A)

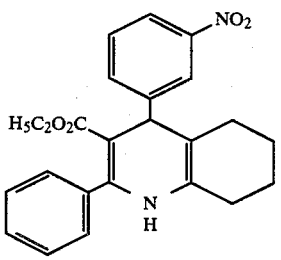

About 100 ml of ethanol are added to 25 g (0.05 mole) of ethyl 8a-morpholino-4-(3-nitrophenyl)-2-phenyl-4a,5,6,7,8,8a-hexahydro-4H-chromene-3-carboxylate in a conical flask (magnetic stirrer). 200 ml of a mixture of 50% of ethanol/50% of concentrated HCl are then added and complete solution is awaited (filtering off any insoluble material).

The mixture is then rendered alkaline with concentrated ammonia and left to cool to room temperature (if necessary adding a little water) and the precipitate is filtered off with suction and recrystallized from ethanol.

Yield: 15 g (74% of theory).
Melting point: 155° C.

The following were prepared analogously to Examples 1 and 2:

Example 3

Ethyl 2-methyl-8a-morpholino-4-(3-nitrophenyl)-4a,5,6,7,8,8a-hexahydro-4H-chromene-3-carboxylate

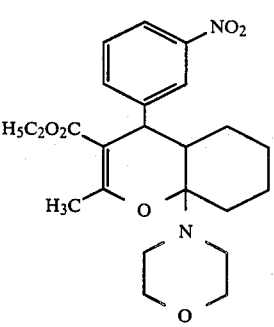

Melting point: 133° C.

Example 4

Ethyl 2-methyl-4-(3-nitrophenyl)-1,4,5,6,7,8-hexahydroquinoline-3-carboxylate (variant A from 3)

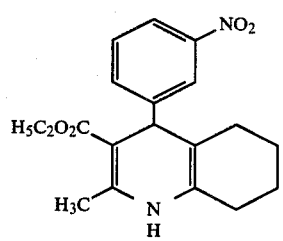

Melting point: 131° C.

Example 5

3-Acetyl-2-methyl-8a-morpholino-4-(3-nitrophenyl)-4a,5,6,7,8,8a-hexahydro-4H-chromene

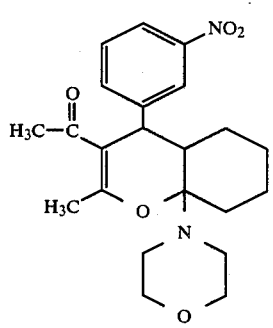

Melting point: 164° C.

Example 6

3-Acetyl-2-melting-4-(3-nitrophenyl)-1,4,5,6,7,8-hexahydroquinoline (variant A from 5)

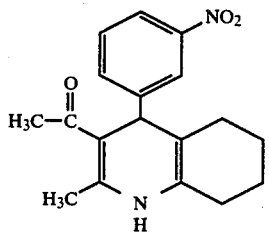

Melting point: 161° C.

Example 7

2-Methyl-8a-morpholino-3-nitro-4-(2-trifluoromethylphenyl)-4a,5,6,7,8,8a-hexahydro-4H-chromene

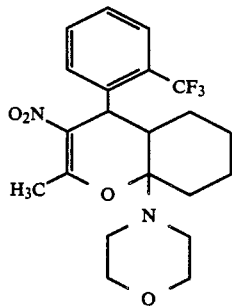

10.4 g (40 mmol) of 2-nitro-1-(2-trifluoromethylphenyl)-but-1-en-3-one and 6.7 g (40 mmol) of 1-morpholinocyclohexene are brought together in 20 ml of ethanol at room temperature. An exothermic reaction takes place and after a short time the product crystallizes in pale yellow crystals as an isomer mixture.

Yield: 13.4 g (77% of theory).

Melting point: 133° C.

Example 8

2-Methyl-3-nitro-4-(2-trifluoromethylphenyl)-1,4,5,6,7,8-hexahydroquinoline (variant B)

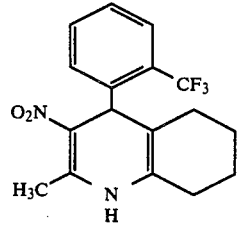

2 g (4.7 mmol) of 2-methyl-8a-morpholino-3-nitro-4-(2-trifluoromethylphenyl)-4a,5,6,7,8,8a-hexahydro-4H-chromene are suspended in 15 ml of ethanol and dissolved with about 3 ml of concentrated aqueous ammonia solution at 30° to 45° C. The pH is then brought to 3 with concentrated hydrochloric acid and the solution is diluted with 5 ml of water and extracted twice with 10 ml of chloroform each time. After the chloroform has been evaporated off, the residue crystallizes in yellow crystals from a little ethanol.

Yield: 580 mg (36% of theory).

Melting point: 222° C. (decomposition).

EXAMPLE 9

1,2-Dimethyl-3-nitro-4-(2-trifluoromethylphenyl)-1,4,5,6,7,8-hexahydroquinoline (variant C)

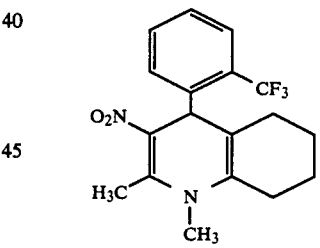

2 g (4.7 mmol) of 2-methyl-8a-morpholino-3-nitro-4-(2-trifluoromethylphenyl)-4a,5,6,7,8,8a-hexahydro-4H-chromene are heated at the reflux temperature in 15 ml of ethanol with 2 g of methylammonium chloride for 6 hours. After cooling, the salts are filtered off with suction, the solution is evaporated, the residue is taken up in chloroform and the mixture is washed with water. The organic phase is dried and concentrated and the residue is chromatographed on silica gel with chloroform with 1% of methanol. Intensely yellow crystals are obtained from ethanol.

Yield: 880 mg (52% of theory).

Melting point: 149° C.

The examples shown in Tables 1 and 2 were prepared by processing analogous to those described:

TABLE 1
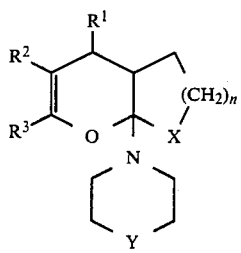
| Example No. | R¹ | R² | R³ | n | X | Y | Melting point [°C.] |
|---|---|---|---|---|---|---|---|
| 10 | 2-CF₃-phenyl | NO₂ | CH₃ | 2 | Bond | O | 128 |
| 11 | 2-Cl-phenyl | CO₂CH(CH₃)₂ | CH₃ | 3 | Bond | O | 120 |
| 12 | 2-CF₃-phenyl | NO₂ | CH₃ | 2 | C=O | O | 132 |
| 13 | 2-Cl-phenyl | CO₂CH(CH₃)₂ | CH₃ | 2 | C=O | O | 172 |
| 14 | 2-Cl-phenyl | CO₂C₂H₅ | CF₃ | 3 | Bond | O | 116 |
| 15 | 2-NO₂-phenyl | CO₂C₂H₅ | CH(CH₃)₂ | 3 | Bond | O | 158 |
| 16 | 2-NO₂-phenyl | CO₂C₂H₅ | C₂H₅ | 3 | Bond | O | 124 |
| 17 | 2-Cl-phenyl | CO₂C₂H₅ | phenyl | 3 | Bond | O | 130 |
| 18 | 2-CF₃-phenyl | CO₂C₂H₅ | phenyl | 3 | Bond | O | 133 |

TABLE 1-continued

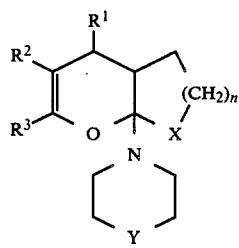

| Example No. | R¹ | R² | R³ | n | X | Y | Melting point [°C.] |
|---|---|---|---|---|---|---|---|
| 19 | 2-methyl-3-benzoyl-6-phenyl thiophene group | $CO_2CH(CH_3)_2$ | $CH_2Cl$ | 3 | Bond | O | 191 |
| 20 | 3-nitrophenyl, 4-methyl | $CO_2C_2H_5$ | $CH_3$ | 9 | Bond | O | 122 |
| 21 | 2-chlorophenyl, 4-methyl | $CO_2C_2H_5$ | $CH_2Cl$ | 3 | Bond | O | 130 |
| 22 | 3-nitrophenyl, 4-methyl | $SO_2CH_3$ | $CH_3$ | 3 | Bond | O | 153 |
| 23 | 2-trifluoromethylphenyl, 4-methyl | $NO_2$ | $CH_3$ | 3 | Bond | $CH_2$ | 116 |
| 24 | 2-trifluoromethylphenyl, 4-methyl | $NO_2$ | $CH_3$ | 9 | Bond | O | Resin |
| 25 | pyridin-3-yl | $COCH_3$ | $CH_3$ | 3 | Bond | O | 120 |
| 26 | 4-hydroxyphenyl, 4-methyl | CN | $CH_3$ | 3 | Bond | O | 161 |
| 27 | pyridin-3-yl | $CO_2C_2H_5$ | $CH_3$ | 3 | Bond | O | Resin |

TABLE 1-continued
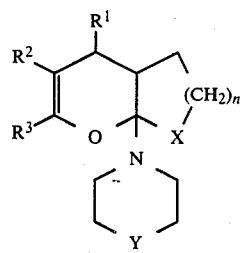
| Example No. | $R^1$ | $R^2$ | $R^3$ | n | X | Y | Melting point [°C.] |
|---|---|---|---|---|---|---|---|
| 28 | 3-NO$_2$-C$_6$H$_4$ | CO$_2$C$_2$H$_5$ | CH$_3$ | 3 | Bond | Bond | 186 |
| 29 | 2-CF$_3$-C$_6$H$_4$ | NO$_2$ | CH$_3$ | 3 | Bond | Bond | 194 |
TABLE 2
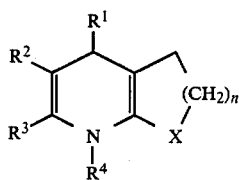
| Example No. | $R^1$ | $R^2$ | $R^3$ | $R^4$ | n | X | Melting point (°C.) |
|---|---|---|---|---|---|---|---|
| 30 | 2-CF$_3$-C$_6$H$_4$ | NO$_2$ | CH$_3$ | H | 3 | Bond | 222 |
| 31 | 2-CF$_3$-C$_6$H$_4$ | NO$_2$ | CH$_3$ | CH$_3$ | 3 | Bond | 149 |
| 32 | 2-CF$_3$-C$_6$H$_4$ | NO$_2$ | CH$_3$ | H | 2 | C=O | 188 |
| 33 | 2-CF$_3$-C$_6$H$_4$ | NO$_2$ | CH$_3$ | C$_2$H$_5$ | 2 | C=O | 168 |
| 34 | 2-Cl-C$_6$H$_4$ | CO$_2$C$_2$H$_5$ | CF$_3$ | H | 3 | Bond | 116 |

TABLE 2-continued
| Example No. | R¹ | R² | R³ | R⁴ | n | X | Melting point (°C.) |
|---|---|---|---|---|---|---|---|
| 35 | 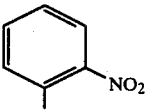 2-NO₂-C₆H₄ | CO₂C₂H₅ | CH(CH₃)₂ | H | 3 | Bond | 158 |
| 36 | 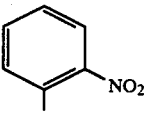 2-NO₂-C₆H₄ | CO₂C₂H₅ | C₂H₅ | H | 3 | Bond | 124 |
| 37 | 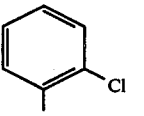 2-Cl-C₆H₄ | CO₂C₂H₅ | C₆H₅ | H | 3 | Bond | 130 |
| 38 | 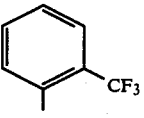 2-CF₃-C₆H₄ | CO₂C₂J₅ | C₆H₅ | H | 3 | Bond | 133 |
| 39 | 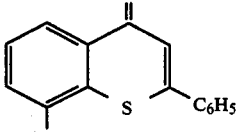 | CO₂—CH(CH₃)₂ | CH₂Cl | H | 3 | Bond | 191 |
| 40 | 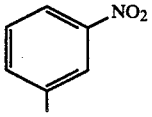 3-NO₂-C₆H₄ | CO₂C₂H₅ | CH₃ | H | 9 | Bond | 122 |
| 41 | 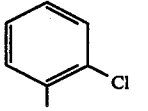 2-Cl-C₆H₄ | CO₂C₂H₅ | CH₂Cl | H | 3 | Bond | 130 |
| 42 | 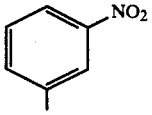 3-NO₂-C₆H₄ | SO₂CH₃ | CH₃ | H | 3 | BOnd | 153 |
| 43 | 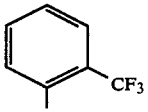 2-CF₃-C₆H₄ | SO₂CH₃ | CH₃ | H | 3 | Bond | 116 |
| 44 | 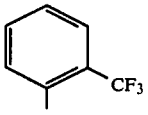 2-CF₃-C₆H₄ | NO₂ | CH₃ | H | 9 | Bond | Resin |

TABLE 2-continued

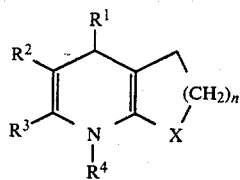

| Example No. | R¹ | R² | R³ | R⁴ | n | X | Melting point (°C.) |
|---|---|---|---|---|---|---|---|
| 45 | (3-pyridyl) | COCH₃ | CH₃ | H | 3 | Bond | 120 |
| 46 | (4-hydroxyphenyl) | CN | CH₃ | H | 3 | Bond | 161 |
| 47 | (3-pyridyl) | CO₂C₂H₅ | CH₃ | H | 3 | Bond | Resin |
| 48 | (3-nitrophenyl) | CO₂C₂H₅ | CH₃ | H | 3 | Bond | Resin |
| 49 | (2-trifluoromethylphenyl) | NO₂ | CH₃ | H | 3 | Bond | Resin |

It is understood that the specification and examples are illustrative but not limitative of the present invention and that other embodiments within the spirit and scope of the invention will suggest themselves to those skilled in the art.

What is claimed is:

1. A compound of the formula

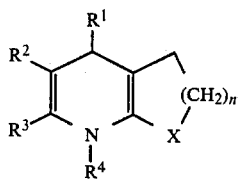

in which

R¹ represents phenyl, thienyl, furyl, pyridyl, benzoxadiazolyl or thiochromenyl, the radicals mentioned optionally contaning 1 or 2 identical or different substituents from the group consisting of $C_1$-$C_4$-alkyl, $C_1$-$C_4$-aloxy, $C_1$-$C_4$-alkylthio, fluorine, chlorine, nitro, cyano, hydroxyl, trifluoromethyl, trifluoromethoxy, difluoromethoxy, fluoromethoxy, phenyl, benzyl, benzyloxy and benzylthio, R² represents hydrogen, nitro, cyano or $C_1$-$C_8$-alkylsulphonyl, or represents the group

wherein

R⁵ represents straight-chain, branched or cyclic $C_1$-$C_8$-alkyl, or represents a group of the formula —O—R⁶, wherein R⁶ represents straight-chain, branched or cyclic $C_1$-$C_{10}$-alkyl, which is optionally interrupted in the chain by one or two oxygen or sulphur atoms and which is optionally substituted by halogen, hydroxy, cyano, nitro, phenyl or pyridyl, or by an amino group optionally being mono- or disubstituted by identical or different substituents from the group consisting of $C_1$-$C_6$-alkyl, $C_6$-$C_{10}$-aryl and $C_7$-$C_{14}$-aralkyl, R³ represents $C_6$-$C_{12}$-aryl, or represents straight-chain or branched $C_1$-$C_8$-alkyl, which is optionally substituted by hydroxyl, halogen or $C_2$-$C_7$-alkanoyloxy, R⁴ represents hydrogen, or represents straight-chain, branched or cyclic C₁-C₈-alkyl, and X represents the group C=O if n represents the number 2 or X represents a direct bond if n represents the number 3, or a physiologically acceptable salt thereof.

2. A compound or salt thereof according to claim 1, in which

R² represents hydrogen, nitro, cyano or C₁-C₆-alkylsulphonyl, or represents the group

wherein

R⁵ represents straight-chain, branched or cyclic C₁-C₆-alkyl, or represents a group of the formula —O—R⁶, wherein R⁶ represents straight-chain, branched or cyclic C₁-C₈-alkyl, which is optionally interrupted in the chain by one or two oxygen atoms and which is optionally substituted by fluorine, chlorine, bromine, hydroxyl, cyano, nitro, phenyl or pyridyl or by an amino group, this amino group optionally being mono- or disubstituted by identical or different substituents from the group consisting of C₁-C₄-alkyl, phenyl or benzyl, R³ represents phenyl, or represents straight-chain or branched C₁-C₆-alkyl, which is optionally substituted by hydroxyl or, fluorine, chlorine, bromine or C₂-C₅-alkanoyloxy, and R⁴ represents hydrogen, or represents straight-chain or branched or cyclic C₁-C₆-alkyl.

3. A compound or salt thereof according to claim 1, in which

R² represents hydrogen, nitro, cyano or C₁-C₄-alkylsulphonyl, or represents the group

wherein

R⁵ represents straight-chain or branched C₁-C₄-alkyl, or represents a group of the formula —O—R⁶, wherein R⁶ represents straight-chain, branched or cyclic C₁-C₆-alkyl, which is optionally interrupted in the chain by an oxygen atom and which is optionally substituted by fluorine, hydroxyl, cyano, phenyl or benzylmethylamino, R³ represents phenyl, or represents straight-chain or branched C₁-C₄-alkyl, which is optionally substituted by hydroxyl, chlorine, bromine or acetyloxy, and R⁴ represents hydrogen, or represents straight-chain or branched C₁-C₄-alkyl.

4. A compound according to claim 1, wherein such compound is ethyl 2-methyl-4-(3-nitrophenyl)-1,4,5,6,7,8-hexahydroquinoline-3-carboxylate of the formula

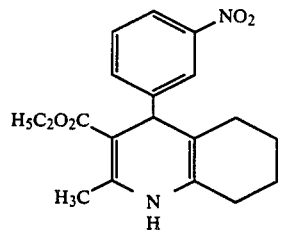

or a physiologically acceptable salt thereof.

5. A compound according to claim 1, wherein such compound is 2-methyl-3-nitro-4-(2-trifluoromethylphenyl)-1,4,5,6,7,8-hexahydroquinoline of the formula

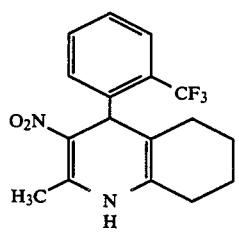

or a physiologically acceptable salt thereof.

6. A compound according to claim 1, wherein such compound is 1,2-dimethyl-3-nitro-4-(2-trifluoromethylphenyl)-1,4,5,6,7,8-hexahydroquinoline of the formula

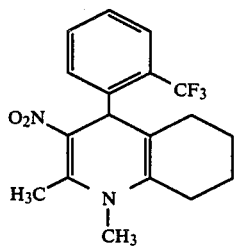

or a physiologically acceptable salt thereof.

7. A compound according to claim 1, wherein such compound is 1-ethyl-2-methyl-3-nitro-8-oxo-4-trifluoromethylphenyl)-1,4,5,6,7,8-hexahydroquinoline of the formula

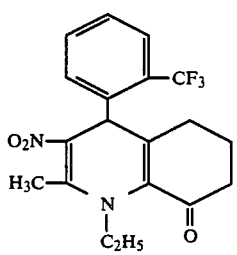

or a physiologically acceptable salt thereof.

8. A compound according to claim 1, wherein such compound is 3-carboethoxy-4-(2-chlorophenyl)-2-phenyl-1,4,5,6,7,8-hexahydroquinoline of the formula

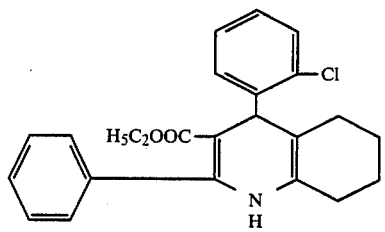

or a physiologically acceptable salt thereof.

9. A compound according to claim 1, wherein such compound is 3-carboethoxy-2-methyl-4-(pyrid-3-yl)-1,4,5,6,7,8-hexahydroquinoline of the formula

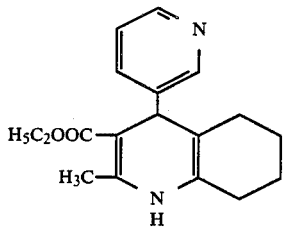

or a physiologically acceptable salt thereof.

10. A circulation-active composition comprising a circulation-active effective amount of a compound or salt according to claim 1 and a diluent.

11. A unit dose of a composition according to claim 10 in the form of a tablet, capsule or ampule.

12. A method of restoring circulation to normalcy which comprises administering to a patient in need thereof a circulation-active effective amount of a compound or salt according to claim 1.

13. The method according to claim 12, wherein such compound is ethyl 2-methyl-4-(3-nitrophenyl)-1,4,5,6,7,8-hexahydroquinoline-3-carboxylate, 2-methyl-3-nitro-4-(2-trifluoromethylphenyl)-1,4,5,6,7,8-hexahydroquinoline, 1,2,-dimethyl-3-nitro-4-(2-trifluoromethylphenyl)-1,4,5,6,7,8-hexahydroquinoline, 1-ethyl-2-methyl-3-nitro-8-oxo-4-trifluoromethylphenyl)-1,4,5,6,7,8-hexahydroquinoline, 3-carboethoxy-4-(2-chlorophenyl)-2-phenyl-1,4,5,6,7,8-hexahydroquinoline or 3-carboethoxy-2-methyl-4-(pyrid-3-yl)-1,4,5,6,7,8-hexahydroquinoline, or a physiologically acceptable salt thereof.

14. A compound or salt according to claim 1, in which $R^2$ represents nitro or $-CO-O-CH_1-C_6$-alkyl, and
$R^3$ represents phenyl or $C_1-C_6$-alkyl.

* * * * *

UNITED STATES PATENT AND TRADEMARK OFFICE
CERTIFICATE OF CORRECTION

PATENT NO. : 4,769,375
DATED : September 6, 1988
INVENTOR(S) : Horst Meyer, et al It is certified that error appears in the above-identified patent and that said Letters Patent is hereby corrected as shown below:

| | |
|---|---|
| Col. 5, line 66 | Delete "or" and substitute --of-- |
| Col. 6, line 37 | Delete "trichloroethyl" and substitute --trichloroethylene-- |
| Col. 11, line 6 | After "3-Acetyl-2-" delete "melting" and substitute --methyl-- |
| Col. 12, line 68 | Delete "processing" and substitute --processes-- |
| Col. 20, Example No. 42, under "X" | Delete "BOnd" and substitute --Bond-- |
| Col. 21, line 62 | Correct --containing-- |
| Col. 21, line 64 | Delete "-aloxy" and substitute -- -alkoxy -- |
| Col. 26, line 27 | Delete "-CH$_1$-" and substitute -- -C$_1$- -- |

Signed and Sealed this

Fourth Day of April, 1989

Attest:

DONALD J. QUIGG

Attesting Officer

Commissioner of Patents and Trademarks